United States Patent
Higueras et al.

(10) Patent No.: US 6,676,663 B2
(45) Date of Patent: Jan. 13, 2004

(54) APPLICATOR DEVICE FOR CONTROLLABLY INJECTING A SURGICAL CEMENT INTO BONES

(76) Inventors: Antonio Pérez Higueras, Rosas de Aravaca, 16, 28023 Madrid (ES); Tomás Martín Valdiviesa, Arturo Soria, 85 - 1° C, 28027 Madrid (ES)

(*) Notice: Subject to any disclaimer, the term of this patent is extended or adjusted under 35 U.S.C. 154(b) by 52 days.

(21) Appl. No.: 09/908,989

(22) Filed: Jul. 19, 2001

(65) Prior Publication Data
US 2003/0018339 A1 Jan. 23, 2003

(51) Int. Cl.⁷ .................. A61B 17/58; A61M 37/00
(52) U.S. Cl. ........................... 606/93; 604/155
(58) Field of Search ................. 606/92, 93, 94; 128/DIG. 12; 222/390; 604/97.02, 97.01, 135, 152, 154, 155, 187, 197, 199, 207, 208, 211, 218

(56) References Cited

U.S. PATENT DOCUMENTS

| | | | | |
|---|---|---|---|---|
| 3,155,090 A | * | 11/1964 | Holter | 600/432 |
| 4,978,335 A | * | 12/1990 | Arthur, III | 604/67 |
| 5,322,511 A | * | 6/1994 | Armbruster et al. | 604/155 |
| 5,611,784 A | * | 3/1997 | Barresi et al. | 604/211 |
| 5,716,345 A | * | 2/1998 | Halbich | 604/207 |
| 5,807,334 A | * | 9/1998 | Hodosh et al. | 604/131 |

FOREIGN PATENT DOCUMENTS

WO   WO 03/000121 A2 *  1/2003

* cited by examiner

Primary Examiner—Pedro Philogene
Assistant Examiner—David Bonderer
(74) Attorney, Agent, or Firm—Klauber & Jackson

(57) ABSTRACT

An applicator device for controllable injecting a cement into bones, particularly, in percutaneous vertebroplasty, comprising an elongated body with an inner axial cavity, a guiding block having an inner thread closing a first end of the axial cavity, a rotatable spin having a central outer thread portion and a distal end emerging from an axial cavity through the guiding block, the spin being axially movable within the axial cavity when being rotated, a syringe holder compartment for tightly holding a syringe body within an axial space being in axial continuation of the axial cavity, the syringe holding compartment comprising a hollow body being releasably fastened by fastening means within at least an end portion of said axial cavity, and at least a first axial rib outwardly protruding from the hollow body, the first axial rib fitting within a complementary first axial slot in said end portion of the axial cavity.

18 Claims, 8 Drawing Sheets

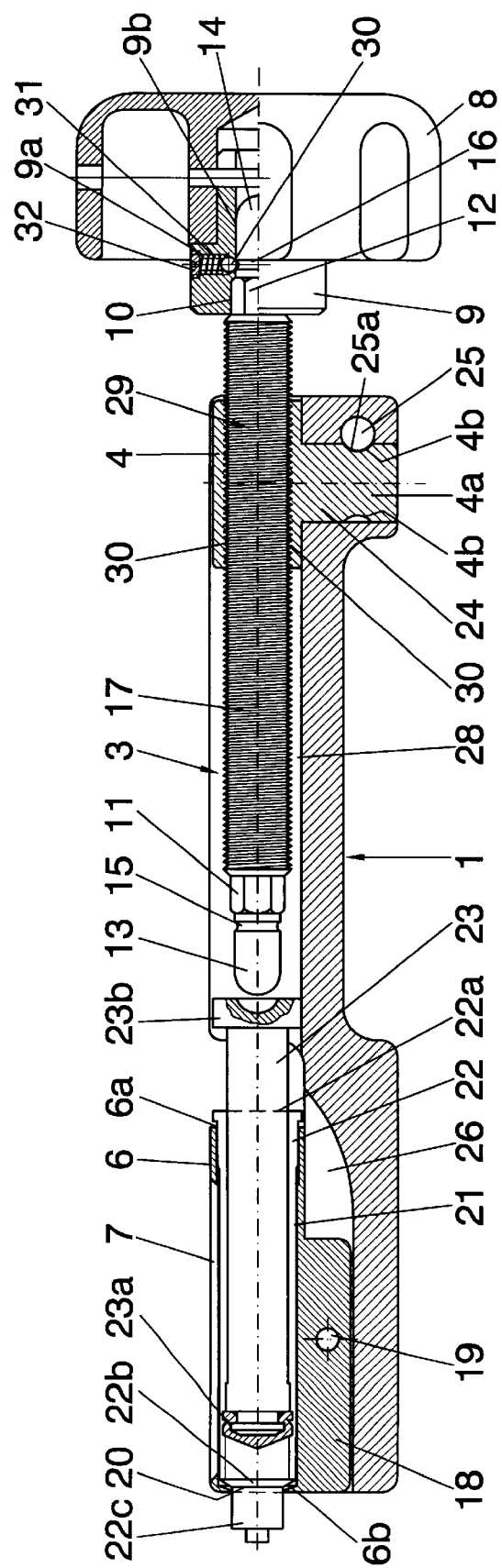
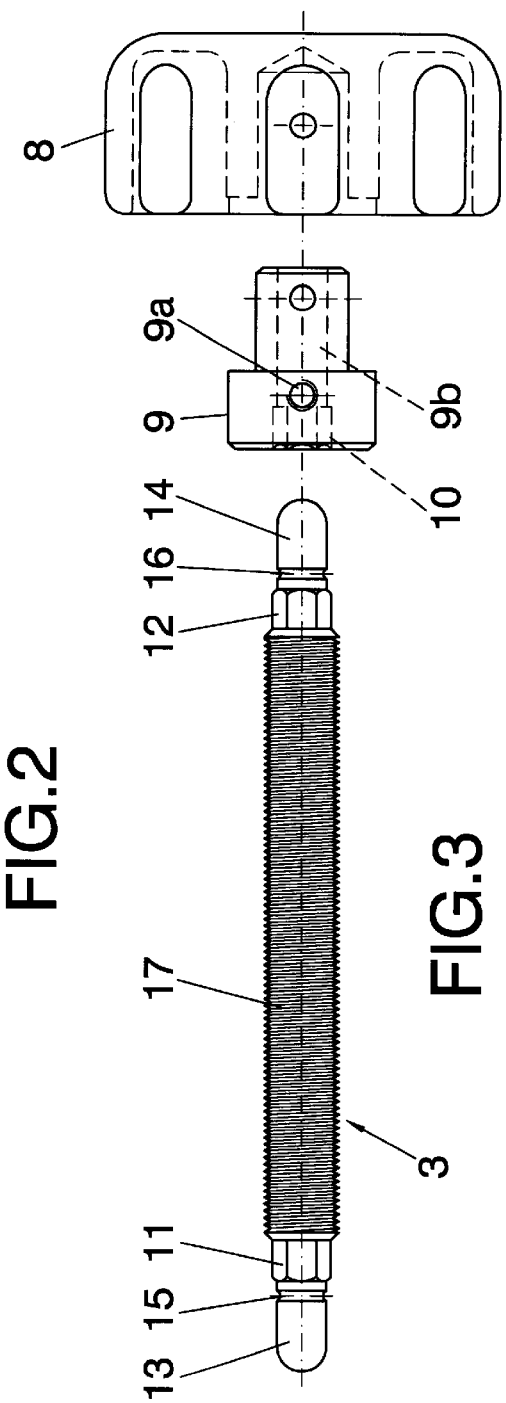
FIG.2
FIG.3

APPLICATOR DEVICE FOR CONTROLLABLY INJECTING A SURGICAL CEMENT INTO BONES

TECHNICAL FIELD

This invention relates to an applicator device for controllably injecting surgical cement into bones, particularly for use in percutaneous vertebroplasty, whereby the applicator device that allows the use of a per se conventional syringe body containing a pastous mass such as a bone cement.

BACKGROUND OF THE INVENTION

Pathological states affecting bones as for example the bone of vertebra of the backbone are rather common. In connection with vertebra, such pathologies may originate from a plurality of origins, the most frequent ones being bone fractures and pathological states such as tumors, osteoporosis etc. leading to at least a partial destruction of the bone structure which in turn results severe pain, in a compression of the spinal cord and may even lead to permanent incapacity of the patients.

Surgical techniques have been developed to provide a certain reconstruction or at least a certain stabilization of the affected bone by non-invasive surgery. These techniques comprise percutaneously applying a hardenable cement mass by injecting the mass into affected areas of the vertebra through a hollow needle of a syringe being introduced through an inner cavity of a previously placed puncturing stylet, the injection being controlled by monitoring the cement mass which may be isotopically marked, by X-ray monitoring means. In view that the cement mass must be injected into the vertebra itself and taking into account the highly dense nature of the cement masses used, high pressures are necessary to force the mass through the hollow needle and into the bone tissue of the vertebra, in this kind of surgery it is difficult to meter exact amounts, to avoid leaking of the cement into areas outside the vertebral area, as for example leaking into the venous locoregional region, the intradiscal region and/or even the pulmonary region, as such leakages may result dangerous and even fatal for the patient being treated. One conventional way of attempting to avoid the leakages, has been to use rather thick needles having rather wide inner channels. Although the use of such thick needles requires less force to be applied compared to the use of conventional needles, they do not permit sufficiently exact metering of the cement in addition to be rather invasive and not allowing accurate local application of the cement.

Applicator devices have been designed to overcome the aforementioned problems related to accurate metering and application of the cement such designs comprising screw means for pushing plungers into syringe-like bodies from which the cement mass is controllably expelled through a needle connected to an outlet of the syringe-like bodies.

Thus, EP-A-1074231 discloses a device for metering a surgical hardenable mass for vertebroplasty comprising a metering body, plunger with a screw-threaded shaft and a plunger head and a rotator knob, the shaft and plunger head being displaceable within the metering body, and a coupling for a manual pump for filling the hardenable mass into a metering body, such that, upon screwing the screw-threaded shaft into the metering boy, the plunger head expels the hardenable mass from the metering device through a hollow needle. This device, albeit allowing a rather accurate metering of a cement mass without requiring much force to expel said mass, has the disadvantages that the cement mass is in direct contact with the inside cavity of the metering body so that sterilization problems may arise and that, should, for example when the device has not been cleaned immediately after use, the cement mass hardens within the metering body and renders the whole device useless.

Spanish Patent EP-2121676-B1 discloses a support for syringes comprising a semicylindrical body having an annular end portion with a guiding block closing the, the guiding block having an inner path with an inner thread, a rotatable spin and a substantially conical end portion opposed to the annular end portion. The spin has an outer thread, a distal end passing through the inner path of the guiding block, and a proximal end protruding into the cavity of the semicylindrical body such that the spin is axially movable within the axial cavity when being rotated upon being screwed and unscrewed within the inner thread of the guiding block. The proximal end of the spin has a discoidal pusher. A per se conventional syringe may be inserted into the space between the conical portion and the discoidal pusher so that, when the spin is actuated, it pushes the plunger of the syringe into the syringe body so that the material contained in the syringe body is expelled. Whilst the applicator device disclosed in Spanish Patent EP-2121676-B1 allows the use of conventional plastic syringes so that hardening of a therein contained cement mass does not render the whole of the device useless, it has the disadvantage that the syringe is not really fixed at the open axial portion of said body, so that when high axial pressures are exerted on the syringe body, the body may deform break and/or be expelled from the semicylindrical body.

DESCRIPTION OF THE INVENTION

The present invention is aimed to overcome the aforementioned disadvantages of prior art applicator device by means of an applicator device for controllably injecting a surgical cement into bones, particularly in percutaneous vertebroplasty, the device comprising an elongated body having a first end portion, a second end portion, a first side wall, a second side wall, and a bottom portion, an axial space between the first side wall, the second side wall and the bottom portion, the axial space having a first end and a second end, a guiding block closing the first end of the axial space and located at said second end portion, the guiding block having an inner path with an inner thread, a rotatable spin having an outer threaded portion, a distal end emerging from the axial space by the first end of the axial space through the inner path of the guiding block, and a proximal end protruding into the axial space, the spin being axially movable within the axial space when being rotated within the inner thread of the guiding block, said proximal end pressing on a plunger into a syringe body when said pin is screwed into said axial space, and a syringe holder compartment for holding the syringe body the syringe body having an open insertion end for insertion of the plunger and an outlet end with a tubular outlet.

According to the invention, the syringe holder compartment is a hollow body being releasably fastened by fastening means to said second end portion of said elongated body, and comprising an axial inner cavity being in axial alignment with said axial space, an open end for insertion of the syringe body by its outlet end, and an abutment end for abutment thereagainst of the outlet end of the syringe body, the abutment end having an opening for said tubular outlet to protrude out of the hollow body. The releasable hollow body has manifold advantages. Thus, it is a first advantage that the periphery of the syringe body is held within the axial cavity of the hollow body such that the wall avoids the syringe body to deform when the standard high pressures for injecting cement into bones are applied. Another advantage is related to the fact that, as well known, standard bone cements as those used in percutaneous vertebroplasty, harden and must harden rather quickly (6–8 minutes maximum) so that, when more than a cement volume of more than one syringe needs to be injected, it becomes essential that the subsequent syringe(s) may be mounted in the applicator device as quickly as possible. In accordance with the invention, the hollow body is that it may be rapidly released from the elongated body when the load of a syringe has been injected into the bone, a new syringe with a further load of cement may be inserted into the hollow body, and the hollow body with the new syringe may be rapidly mounted in the applicator. Still another advantage is that, to make the applicator device suitable for using syringes of different dimensions, a plurality of hollow bodies each having an inner cavity with dimensions being adapted to a different type of syringe may be designed, so that various types of syringes may be used in the same applicator device.

The hollow body may comprise an elongated axial slot penetrating through at least one of an upper or a lateral wall portion of said hollow body, said axial being coaxial to the axial cavity. Such elongated slot or slots, in addition to allow viewing a lateral portion of the syringe body and the position of the plunger head within the syringe body, may be designed such that it also constitutes a section into which the syringe body may deform when excessive pressure is applied. When deforming, the syringe body radially separates from the plunger head so that the cement mass contained in the syringe flows backwards over the plunger head when still more is applied. Thus, the axial slot may act also have the function of a kind of security valve mechanism.

In accordance with one embodiment of the invention, the fastening means comprise an axial rib downwardly protruding from the hollow body, the axial rib fitting within a complementary axial recess within said bottom portion at said second end portion of the elongated body, and at least two lateral projections emerging respectively from lateral portions of said rib, said projections respectively fitting within holding slots in opposed wall portions of said recess. In this embodiment, the holding slots respectively comprise at least first sections that extend into the wall portions in a direction being at least perpendicular to said axial space such that when said projections are fitted within said holding slots, axial movement of the hollow body towards said second end of the elongated body is prevented. Thus, the holding slots may be angular slots respectively comprising, in addition to said first sections, second sections being coaxial with said axial space and extending towards said second end of the elongated body.

In another embodiment of the invention, the hollow body fits between opposed sections of said side walls of the elongated body and the fastening means comprise two lateral projections emerging respectively from opposed lateral portions of said hollow body, said projections respectively fitting within holding slots in said opposed sections. In this embodiment, the holding slots also comprise at least first sections that respectively extend into said opposed sections of the side walls in a direction being at least perpendicular to said axial space such that when said projections fit within said holding slots, axial movement of the hollow body towards said second end of the elongated body is prevented, whereby the slots may further be angular slots respectively comprising, in addition to said first sections, second sections being coaxial with said axial space and extending towards said second end of the elongated body. Also in this embodiment, the hollow body may additional comprise an axial rib of the type described herein above, i.e. an axial rib protruding downwardly from the hollow body, and fitting within the complementary axial recess within said bottom portion at said second end portion of the elongated body.

The guiding block for said spin, may be releasably fixed within said axial space, to said first end portion of said bottom portion of said elongated body. The releasable nature of the block, allows, inter alia, removal of the block for the purpose of an easier and better cleaning and sterilization of the applicator device. The guiding block may comprise a main body and a protruding portion emerging from the main body, said protruding portion fitting within a hole in said first end portion of said bottom portion. Preferably, the protruding portion is releasably blocked in said hole by blocking means, comprising a straight passage extending through said bottom portion of the elongated body from one side surface to an opposite side surface, said passage comprising a section having an open side section coinciding with said hole, a least one lateral recess in the protruding portion, said lateral recess facing the open side section of the passage, and a blocking bolt fitting within the passage, the bolt having a first bolt head and a second bolt head for retaining the bolt within the passage, and a narrowed portion. The bolt is slidable within said passage between a blocking position in which the narrowed portion of said protruding portion is not located in said open side section of the passage so that the bolt fits within said lateral recess, and a release position in which said narrowed portion is located in said open side section such that said protruding portion may be extracted from said hole. A helicoidal spring is arranged around the bolt between said first bolt head and said passage for resiliently holding the bolt in the blocking position. So as to avoid the first and second bolt heads to excessively protrude from the side surfaces of the elongated body of the actuator device, the straight passage may have a first widened end portion for at least partially housing said helicoidal spring and a second widened end portion for housing said second bolt head.

For screwing and unscrewing the spin within the thread of the guiding block, the distal end of the spin may be fixedly or releasably coupled to a rotating knob. So as to provide firm coupling of the rotating knob the spin may comprise a polygonal portion between said distal end and said outer thread. Said polygonal portion becomes inserted within a complementary polygonal opening within a coupling element inserted in the knob body. On the other hand, to provide a point of maximum pressure on the plunger, the proximal end of the spin may be convex.

In a preferred embodiment of the invention, the spin comprises a first half section comprising said proximal end and a first half of said outer threaded portion and a second half section comprising said distal end and a second half of said outer threaded portion, the first half and the second half being symmetric with regard to an axis being perpendicular in respect of a longitudinal axis of the spin, the distal end of the spin is releasably coupled to a rotating knob, and the guiding block is releasably coupled to the elongated body. This preferred embodiment has the further advantage that, replacement of an emptied syringe by a new full one may be further accelerated for the following reasons. When syringe has been emptied, the proximal end of the spin has pushed the plunger into the syringe body so that, to allow mounting a hollow body containing a new full syringe from which the plunger protrudes into the axial space more than did the plunger of the emptied syringe, the proximal end of the must be retracted to allow the plunger of the full syringe fitting within the axial space. Having to unthread the spin until its proximal end is retracted enough to allow mounting the hollow body with the full syringe involves some time. According to this preferred embodiment, practically no time for unthreading the spin is required inasmuch it is basically sufficient to release the guiding block, uncouple the rotatable knob from the distal end of the spin, to reinsert the guiding block in a reverse position such that the previously proximal end of the spin becomes the distal end and vice versa, and to couple the rotating knob to what has become the distal end of the spin.

In this embodiment, the spin may further comprise a first polygonal portion between said proximal end and the outer thread, and a second polygonal portion between said distal end and said outer thread, and the spin's proximal as well as its distal end may be convex. These polygonal portions are for coupling the spin to a rotatable knob via a coupling element, as described herein above.

Preferably, in view of the high pressures applied when the cement is forced out of the syringe when the spin is screwed against the plunger, the plunger body is made of hard and undeformable metal, and may further have a widened end portion. This end portion may have a perimeter being designed to be radially guided within said axial space.

The various elements of the applicator device may be made of one or more metals such as steel, steel alloys, aluminum, aluminum alloys etc. in a manner known per se. Preferably, the guiding block is made of strong plastic material offering a certain resistance to threading of the spin.

BRIEF DESCRIPTION OF THE DRAWING

Further features of the invention will be hereafter described on the basis of embodiments shown in the figures attached to this specification. In these figures.

FIG. 2 is a partially sectioned side view of the applicator device shown in FIG. 1 with a syringe mounted in the device;

FIG. 3 is a side view of the spin, the rotating knob and of the means for coupling the distal end of the spin to the knob in the embodiment shown in FIGS. 1 and 2;

EMBODIMENTS OF THE INVENTION

FIGS. 1 to 9 illustrate a first embodiment of the applicator device according to the invention.

Figure 1:
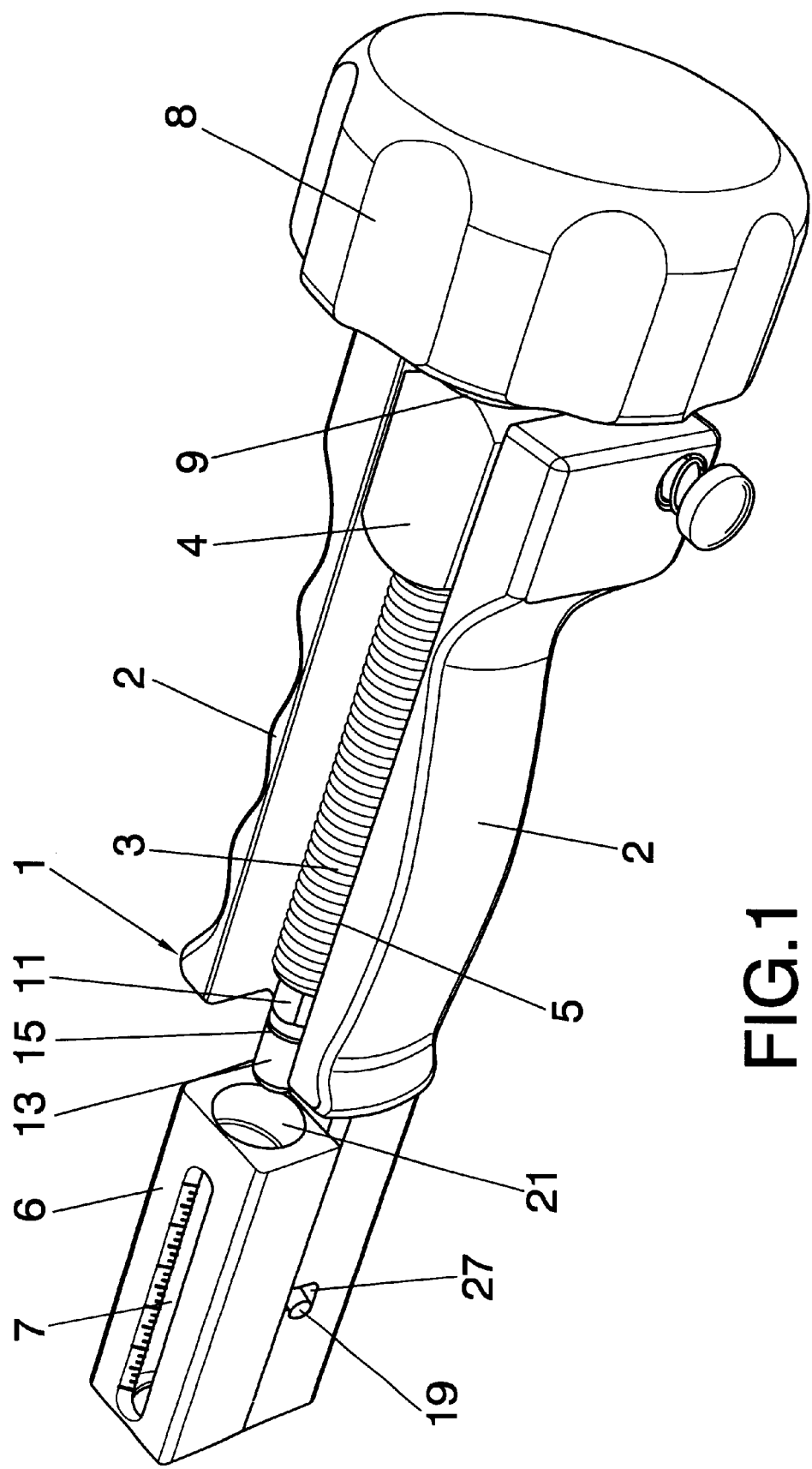
FIG. 1 is a top view in profile of the applicator device in accordance with an embodiment of the invention.

As shown in FIG. 1 the applicator device of the invention comprises an elongated body 1 comprising side walls 2 and an axial space 5 defined between the side walls 2. The axial space 5 is closed at one end by a guiding body 3. The guiding body 3 is located between the side walls 2 at a first end of the elongated body 1. A spin 3 guided through the guiding block 4 extends through the axial space 5. In axial continuation of the axial space 5, there is an axial inner cavity 21 of a hollow body 6, said hollow body 6 for holding a syringe body (not shown in FIG. 1) within its inner cavity 21. According to the position shown in FIG. 1, the proximal end 13 of the spin 3 is located in the proximity of the hollow body 6 whilst its distal end is coupled to a knob 8 by means of a coupling body 9. The outer surface of the side walls 2 are ergonomically shaped to enable the device being firmly, comfortably and securely gripped by surgeon.

FIG. 2 shows that the hollow body 6 has an axial rib 18 provided with a lateral projection 19, an open end 6a and an abutment end 6b. The axial rib fits within an axial slot 26 in a bottom portion 28 of the elongated body 1. The hollow body 6 holds a syringe body 22 with a plunger 23 inserted into the syringe body 22 by an insertion end 22a thereof. The syringe body further has an outlet end 22b abutting against the hollow body's abutment end 6b with a tubular outlet 22c that emerges from the hollow body 6 through an opening 20 in the abutment end 22b. The plunger 23 has a head 23a and a widened end portion 23b that is radially guided within the axial space defined between the bottom portion 28 and the side walls of the elongated body 1. The spin 3 that extends within the axial space comprises a proximal end 13 and a distal end 14 and an outer threaded portion 17. Between the spin's proximal end 13 and its outer threaded portion 17, there are a first annular recess 15 and a first polygonal portion 11 whilst between the spin's distal end 14 and its outer threaded portion 17, there are a second annular recess 16 and a second polygonal portion 12. The spin's distal end 14 is inserted within an axial path 9b of the coupling element 9 such that the second polygonal portion 12 fits within a complementary polygonal opening 10 and the second annular recess 16 is positioned in correspondence with a per se known coupling mechanism comprising a spring 31 compressed between a retaining element 32 and a ball 30 being housed in a radial perforation 9a of the coupling element 9, such that a part of the ball 30 resiliently protrudes into the axial path 9b. The spin 3 passes through an inner path 29 of the guiding block 4 such that the spin's threaded portion 17 threads within an inner thread 30 in the inner path 29. The guiding block 4 has a protruding portion 4a that fits within a hole 24 in the bottom portion 28 of the elongated body 1. The protruding portion 4a has a recess 4b at a position that corresponds to an open side 25a of a straight passage 25 that passes through the elongated body 1.

FIG. 3 shows with some more details the aforementioned features of the spin 3 and of the coupling element 9.

Figure 4:
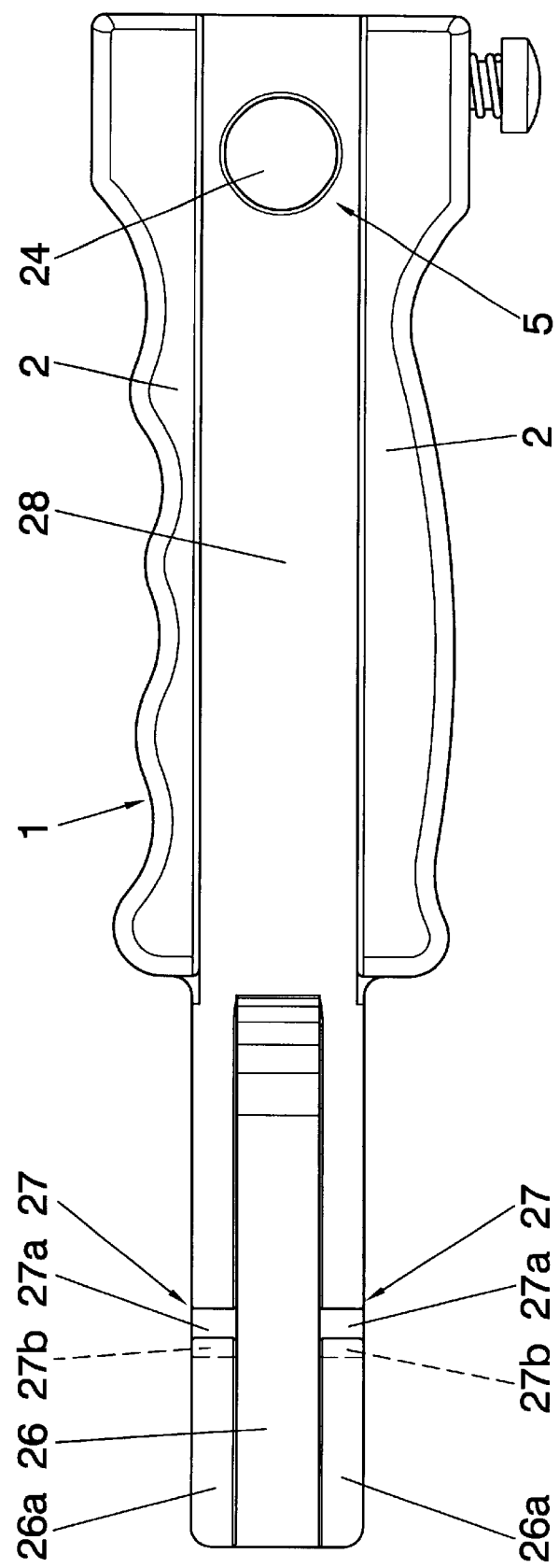
FIG. 4 is a top plan view of the applicator device shown in FIG. 1.
Figure 8:
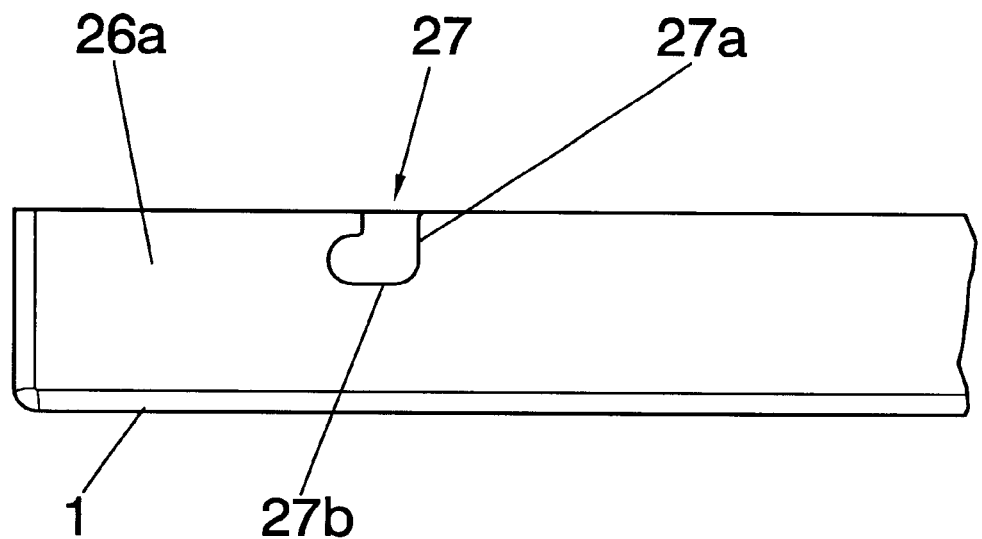
FIG. 8 is a partial side view of the applicator device as shown in FIG. 4.

As shown in FIGS. 4 and 8, the axial recess 26 for insertion of the hollow body shown in FIGS. 1 and 2 is limited between side walls 26a comprising holding slots 27 comprising each a first section 27a that penetrates orthogonally into the side wall 26a and second section 27b that extends coaxially with the side wall 26a.

Figure 5:
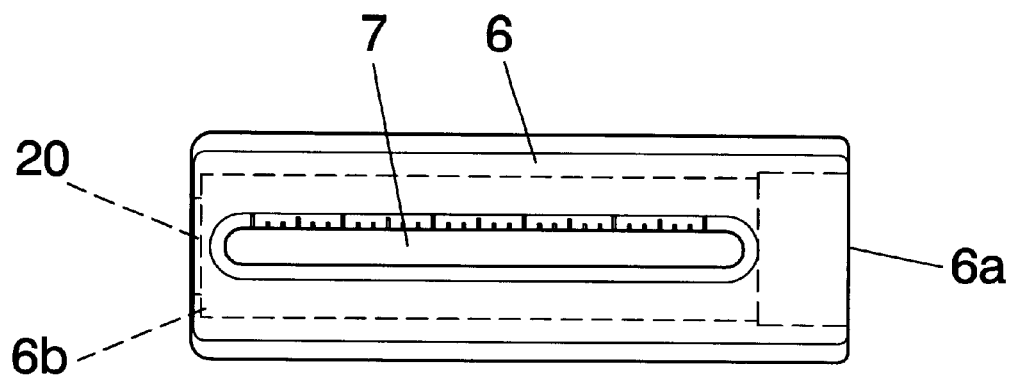
FIG. 5 is a top plan view of the hollow body of the applicator device shown in FIG. 1.
Figure 6:
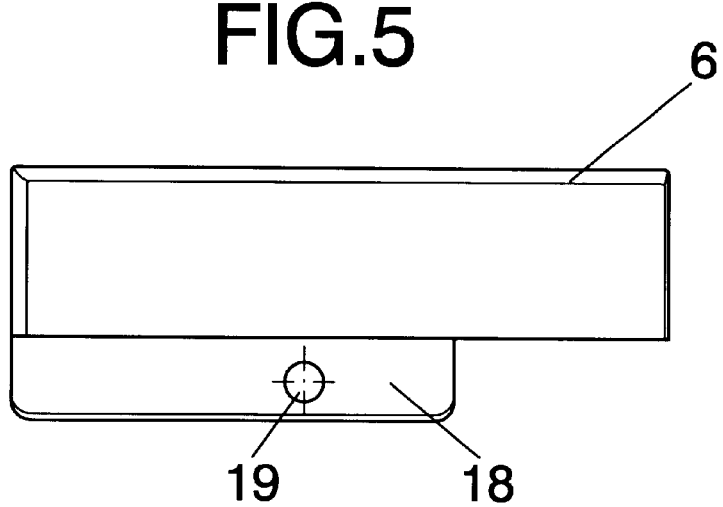
FIG. 6 is a side view of the hollow body of the applicator device shown in FIG. 1.
Figure 7:
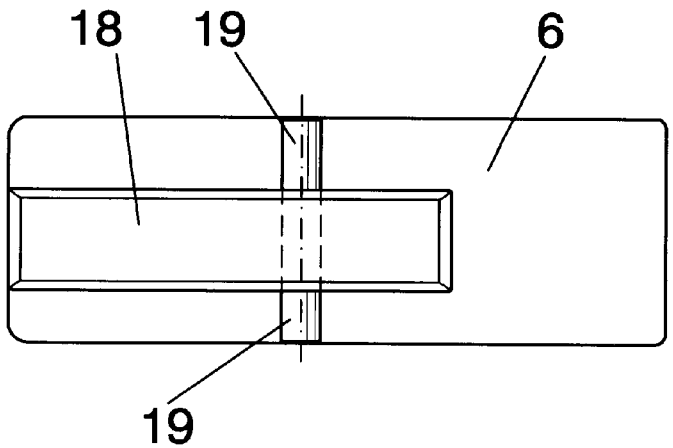
FIG. 7 is a bottom view of the hollow body of the applicator device shown in FIG. 1.

FIGS. 5 to 7 show with some more detail the hollow body of FIGS. 1 and 2. Thus, the hollow body's upside has an axial slot 27 and its bottom is provided with an axial rib 18 with lateral projections 19. The lateral projections 19 may be, for example, the end portions of a metal pin fixed within a perforation in the rib.

Figure 9:
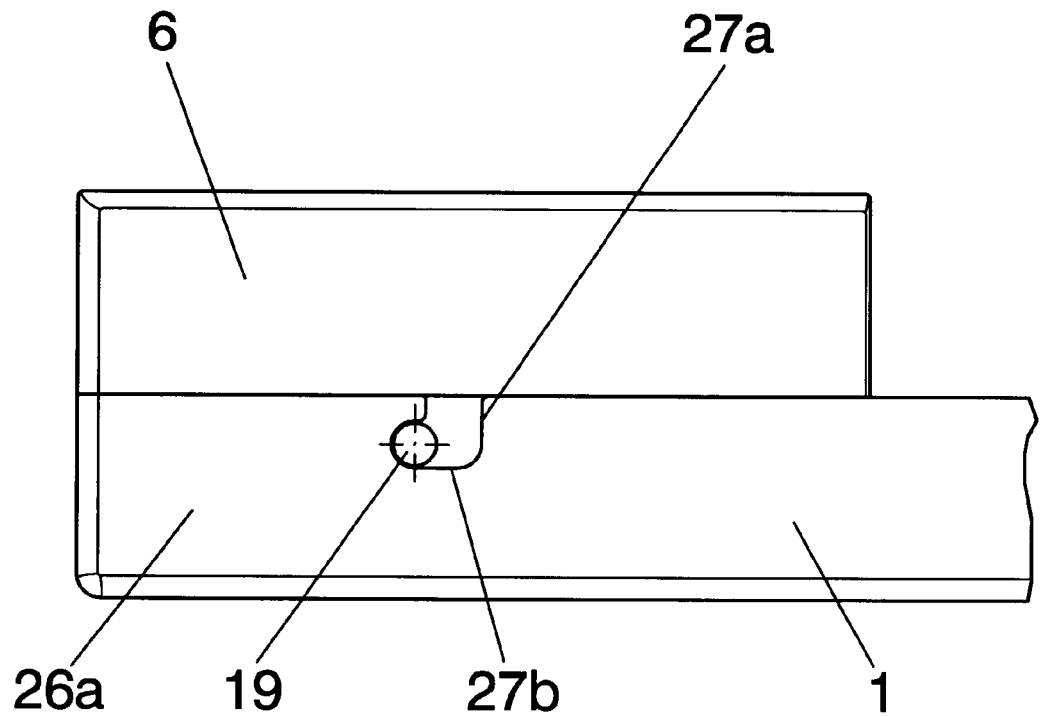
FIG. 9 is a side view of the applicator device as shown in FIG. 8 with the hollow body shown in FIGS. 5 to 6 mounted on the applicator device.
Figure 10:
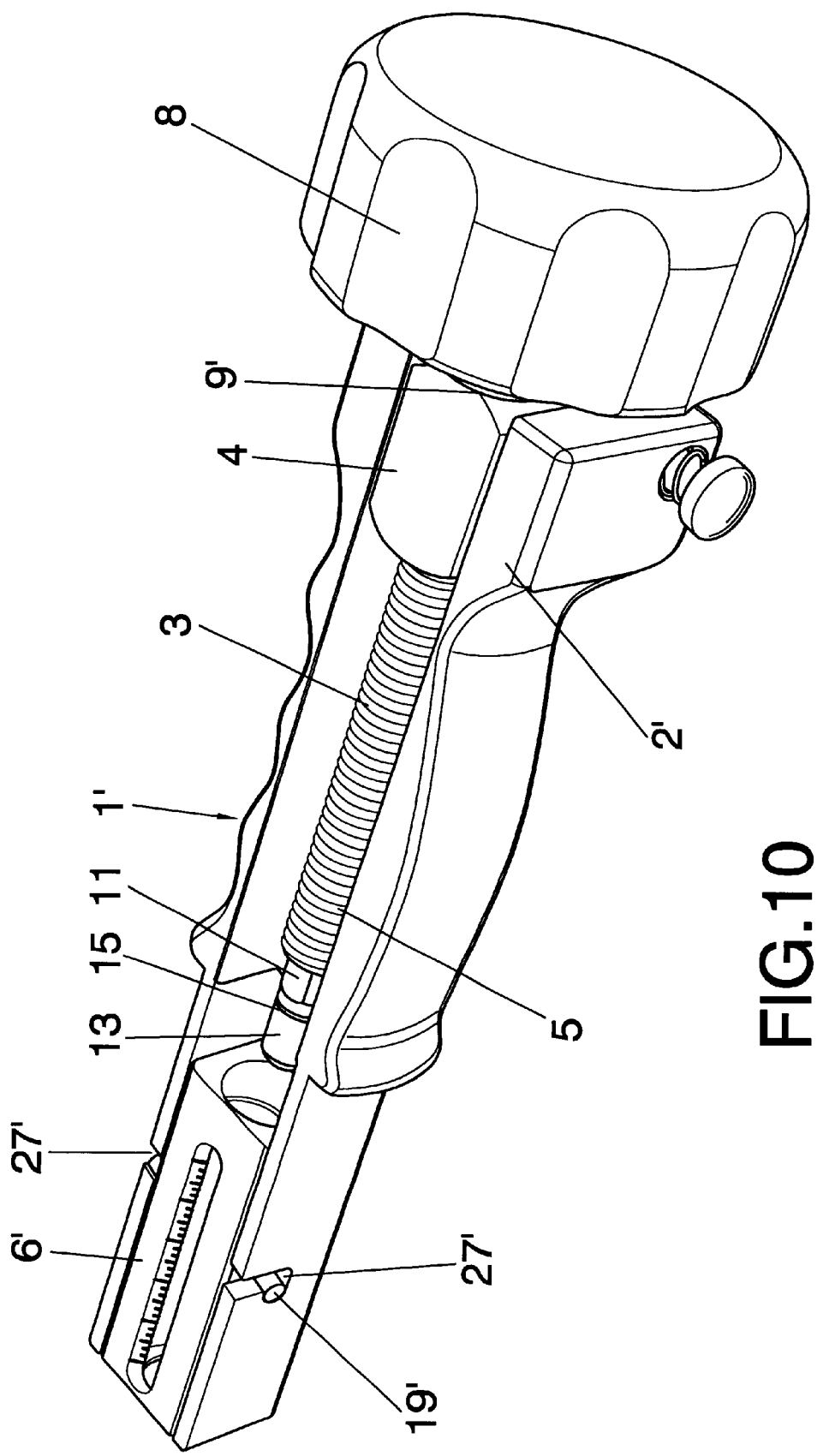
FIG. 10 is a top view in profile of the applicator device in accordance with another embodiment of the invention.
Figure 11:
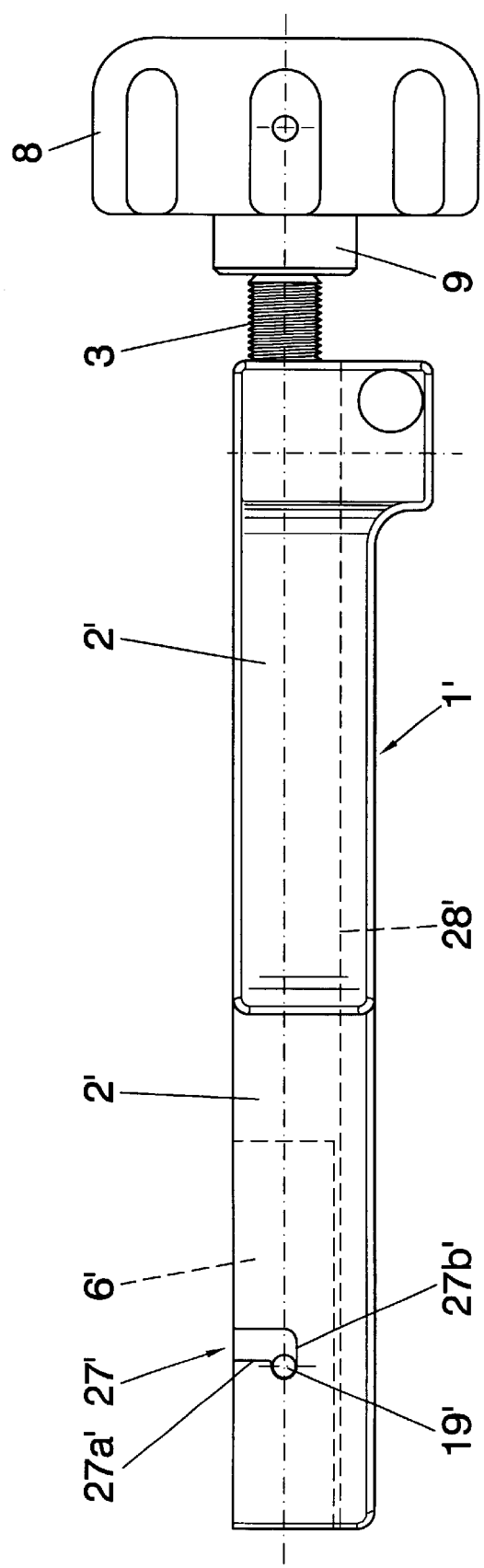
FIG. 11 is a side view of the applicator device shown in FIG. 10.
Figure 12:
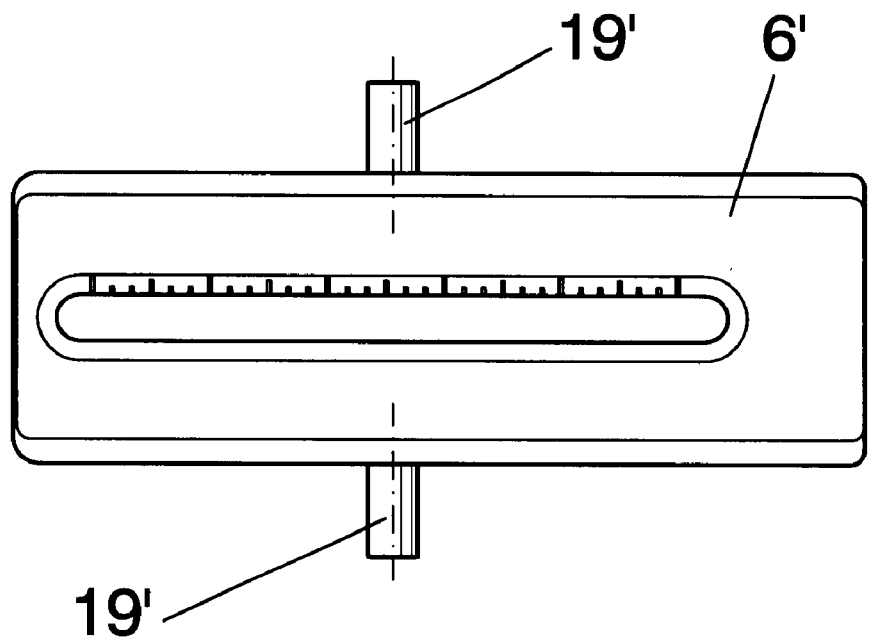
FIG. 12 is a top plan view of the hollow body of the applicator device shown in FIG. 10.
Figure 13:
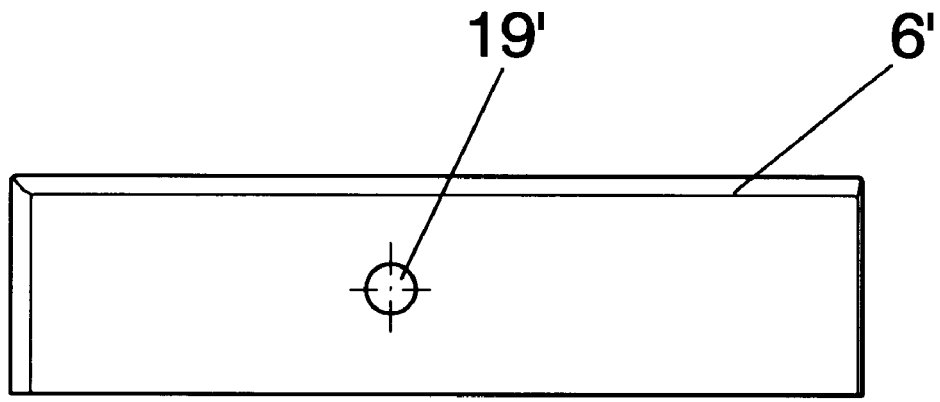
FIG. 13 is side view of the hollow body of the applicator device shown in FIG. 10.

As shown in FIG. 9 the hollow body 6 is mounted on the elongated body 1 such that its bottom portion comes to rest on the side walls 26a and each of the lateral projections 19 of its rib becomes placed within the second section 27b of each slot 27.

FIGS. 10 to 13 show a second embodiment of the applicator device of the invention. This second embodiment differs from the first embodiment shown in FIGS. 1 to 9, in that the elongated body 1' has a flat bottom 28' without the axial recess 26 of the first embodiment, and in that the elongated body's side walls extend until the end of the elongated body 1' such that the hollow body 6' having lateral projections 19' emerging from its lateral surfaces, is mounted between the side walls 2'. For fastening the hollow body 6', the holding slots 27' comprising each a first section 27a' and a second section 27b' are provided in the side walls 2' such that the lateral projections 19' of the hollow body 6' come to rest on the second sections 27b' of the holding slots 27'.

What is claimed is:

1. An applicator device for controllably injecting a cement into a bone, the device comprising an elongated body having a first end portion, a second end portion, a first side wall, a second side wall, and a bottom portion, an axial space between the first side wall, the second side wall and the bottom portion, the axial space having a first end and a second end, a guiding block closing the first end of the axial space and located at said second end portion, the guiding block having an inner path with an inner thread, a rotatable spin having an outer threaded portion, a distal end emerging from the axial space by the first end of the axial space through the inner path of the guiding block, and a proximal end protruding into the axial space, the spin being axially movable within the axial space when being rotated within the inner thread of the guiding block, said proximal end pressing a plunger into a syringe body when said pin is screwed into said axial space, a syringe holder compartment, for holding the syringe body having an open insertion end for insertion of the plunger, and an outlet end with a tubular outlet, the syringe body containing the cement, wherein the syringe holder compartment is a hollow body being releasably fastened by fastening means to said second end portion of said elongated body and comprising an axial inner cavity being in axial alignment with said axial space, an open end for insertion of the syringe body by its outlet end, and an abutment end for abutment thereagainst of the outlet end of the syringe body, the abutment end having an opening for said tubular outlet to protrude out of the hollow body, and wherein the fastening means comprise an axial rib downwardly protruding from the hollow body, the axial rib fitting within a complementary axial recess within said bottom portion at said second end portion of the elongated body, at least two lateral projections emerging respectively from lateral portions of said rib, said projections respectively fitting within holding slots in opposed wall portions of said recess, whereby the holding slots respectively comprise at least first sections that extend into the wall portions in a direction being at least perpendicular to said axial space such that when said projections are fitted within said holding slots, axial movement of the hollow body towards said second end of the elongated body is prevented.

2. An applicator device according to claim 1, wherein said holding slots are angular slots respectively comprising, in addition to said first sections, second sections being coaxial with said axial space and extending towards said second end of the elongated body.

3. An applicator device according to claim 1, wherein said guiding block for said spin, fixed within said axial space, to said first end portion of said bottom portion of said elongated body.

4. An applicator device according to claim 1, wherein said guiding block or said spin, comprises a main body and a protruding portion emerging from the main body, said protruding portion fitting within a hole in said first end portion of said bottom portion.

5. An applicator device according to claim 1, wherein said guiding block for said spin comprises a main body and a protruding portion emerging from the main body, said protruding portion fitting within a hole in said first end portion of said bottom portion, and wherein said protruding portion is releasably blocked in said hole by blocking means, the blocking means comprising a straight passage extending through said bottom portion of the elongated body from one side surface to an opposite side surface, said passage comprising a section having an open side section coinciding with said hole, a least one recess in the protruding portion, said lateral recess facing the open side section of the passage, a blocking bolt fitting within the passage, the bolt having a first bolt head and a second bolt head for retaining the bolt within the passage, and a narrowed portion, the bolt being slidable within said passage between a blocking position in which the narrowed portion of said protruding portion is not located in said open side section of the passage so that the bolt fits within said lateral recess, and a release position in which said narrowed portion is located in said open side section such that said protruding portion may be extracted from said hole, a helicoidal spring arranged around the bolt between said first bolt head and said passage for resiliently holding the bolt in the blocking position.

6. An applicator device according to claim 5, wherein said straight passage has a first widened end portion for at least partially housing said helicoidal spring and a second widened end portion for housing said second bolt head.

7. An actuator device according to claim 1, wherein said spin comprises a first half section comprising said proximal end and a first half of said outer threaded portion and a second half section comprising said distal end and a second half of said outer threaded portion, the first half and the second half being symmetric with regard to an axis being perpendicular in respect of a longitudinal axis of the spin, and wherein said distal end of the spin is releasably coupled to a rotating knob.

8. An applicator device according to claim 7, wherein the spin further comprises a first polygonal portion between said proximal end and the outer thread, and a second polygonal portion between said distal end and said outer thread.

9. An applicator device according to claim 1, wherein the spin further comprises a polygonal portion between said distal end and said outer thread.

10. An applicator device according to claim 1 wherein said proximal end of the spin is convex.

11. An applicator device according to claim 1, wherein said distal end of the spin convex.

12. An applicator device according to claim 1, wherein said distal end of the spin is fixedly coupled to a rotating knob.

13. An applicator device according to claim 1, wherein said distal end of the spin is releasably coupled to a rotating knob.

14. An applicator device according to claim 1, wherein said plunger has an end widened end portion which is radially guided within said axial space.

15. An applicator device according to claim 1, wherein said hollow body comprises elongated axial slot penetrating through at least one wall portion selected among an upper and lateral wall portions of said hollow body, said axial being coaxial to the axial cavity.

16. An applicator device, for controllably injecting a cement into a bone, the device comprising an elongated body having a first end portion, a second end portion, a first side wall, a second side wall, and a bottom portion, an axial space between the first side wall, the second side wall and the bottom portion, the axial space having a first end and a second end, a guiding block closing the first end of the axial space and located at said second end portion, the guiding block having an inner path with an inner thread, a rotatable spin having an outer threaded portion, a distal end emerging from the axial space by the first end of the axial space through the inner path of the guiding block, and a proximal end protruding into the axial space, the spin being axially movable within the axial space when being rotated within the inner thread of the guiding block, said proximal end pressing a plunger into a syringe body when said pin is screwed into said axial space, a syringe holder compartment, for holding the syringe body having an open insertion end for insertion of the plunger, and an outlet end with a tubular outlet, the syringe body containing the cement, wherein the syringe holder compartment is a hollow body being releasably fastened by fastening means to said second end portion of said elongated body and comprising an axial inner cavity being in axial alignment with said axial space, an open end for insertion of the syringe body by its outlet end, and an abutment end for abutment thereagainst of the outlet end of the syringe body, the abutment end having an opening for said tubular outlet to protrude out of the hollow body, wherein the hollow body fits between opposed sections of said side walls of the elongated body and wherein the fastening means comprise two lateral projections emerging respectively from opposed lateral portions of said hollow body, said projections respectively fitting within holding slots in said opposed sections of side walls of the axial space, said holding slots comprising at least first sections that respectively extend into said opposed sections of the side walls in a direction being at least perpendicular to said axial space such that when said projections fit within said holding slots, axial movement of the hollow body towards said second end of the elongated body is prevented.

17. An applicator device according to claim 16, wherein said slots are angular slots respectively comprising, in addition to said first sections, second sections being coaxial with said axial space and extending towards said second end of the elongated body.

18. An applicator device according to claim 16, the hollow body further comprises an axial rib downwardly protruding from the hollow body, the axial rib fitting within a complementary axial recess within said bottom portion at said second end portion of the elongated body.

* * * * *